(12) United States Patent
Lee (10) Patent No.: US 6,503,906 B1
(45) Date of Patent: Jan. 7, 2003

(54) METHOD FOR OPTIMIZING CIPROFLOXACIN TREATMENT OF ANTHRAX-EXPOSED PATIENTS ACCORDING TO THE PATIENT'S CHARACTERISTICS

(76) Inventor: Ren-Jin Lee, 10845 Outpost Dr., Gaithersburg, MD (US) 20878

( * ) Notice: Subject to any disclaimer, the term of this patent is extended or adjusted under 35 U.S.C. 154(b) by 0 days.

(21) Appl. No.: 10/079,091

(22) Filed: Feb. 21, 2002

(51) Int. Cl.$^7$ ............................................ A61K 31/495
(52) U.S. Cl. ........................... 514/235.05; 514/235.07; 514/235.08; 514/885
(58) Field of Search ....................... 514/235.05, 235.07, 514/235.08, 885

(56) References Cited

U.S. PATENT DOCUMENTS 4,670,444 A * 6/1987 Grohe et al. ................. 514/300

* cited by examiner

*Primary Examiner*—Frederick Krass (57) ABSTRACT

The present invention relates to a method for optimizing ciprofloxacin treatment of anthrax-exposed patients according to the patient's characteristics. More particularly, the invention optimizes the survival outcome of a ciprofloxacin treatment for an anthrax-exposed patient, with the ciprofloxacin dose regimen adjusted according to the patient's characteristics, including age, body weight, gender, and renal function.

9 Claims, 6 Drawing Sheets

DRAWINGS

METHOD FOR OPTIMIZING CIPROFLOXACIN TREATMENT OF ANTHRAX-EXPOSED PATIENTS ACCORDING TO THE PATIENT'S CHARACTERISTICS

CROSS-REFERENCE TO RELATED APPLICATIONS

Reference Cited: U.S. Pat. No. 4,670,444; June, 1987; Grohe et al,; 514/300.

BACKGROUND OF THE INVENTION

1. Field of the Invention

The present invention relates to a method for optimizing ciprofloxacin treatment of anthrax-exposed patients according to the patient's characteristics. More particularly, the invention optimizes the survival outcome of a ciprofloxacin treatment for an anthrax-exposed patient, with the ciprofloxacin dose regimen adjusted according to the patient's characteristics, including age, body weight, gender, and renal function.

2. Description of the Related Art

The effectiveness of ciprofloxacin treatment for anthrax may significantly rely on the adequacy of the antibiotic regimen. The regimens of ciprofloxacin currently recommended for treating anthrax are based only on animal survival data and minimum pharmacokinetic information [Physician's Desk Reference, 2001]. Due to the lack of human data reviewed in the prior art, a fixed regimen has been recommended for all patients, namely 500 mg twice daily oral dose.

Even with the fact that the effectiveness of ciprofloxacin against most other infectious organisms is over 80% [Physician's Desk Reference, 2001] at the recommended doses, the survival rate of anthrax patients treated with the drug remains relatively low (50~60% in the US 2001 outbreak [CDC MMWR Weekly, 2001]).

Thus, it is desirable to improve and optimize the currently recommended ciprofloxacin regimen in order to increase the patient survival rate. It is therefore necessary to determine the survival rates of anthrax-exposed patients treated with different ciprofloxacin regimens and select the optimal treatments. One possible approach to obtain the survival data is to conduct human experiments to investigate the effectiveness of various dose regimens in different patient populations. However, this approach is not practical due to the ethical reason.

3. Information Disclosure

Ciprofloxacin and its quinolone family are a series of potent antimicrobial agents with a broad spectrum of antimicrobial activities. The quinolone family is active against a variety of human and veterinary pathogens, including both gram-positive and gram-negative bacteria. Ciprofloxacin is disclosed in U.S. Pat. No. 4,670,444, issued Jun. 2, 1987 to Bayer Aktiengesellschaft.

BRIEF SUMMARY OF THE INVENTION

The present invention seeks to overcome the drawbacks inherent in the prior art by providing new methods for improving and optimizing the ciprofloxacin regimen for treating anthrax-exposed patients.

Therefore, one object of the present invention is to provide a method to optimize the survival rate of ciprofloxacin treatment for anthrax in different patient populations.

It is known that a complete bacteria eradication by ciprofloxacin usually occurs within several days after the initiation of the antibiotic treatment. Therefore, during the first few days of the antibiotic treatment, the patients may remain culture-positive. Since the deaths of the patients infected with anthrax are associated with the presence of the bacteria in the patient's body, it is plausible that the mortality rate of the ciprofloxacin-treated and yet culture-positive patients is similar to the mortality rate of the controlled patients who receive no effective treatment, if significant amounts of anthrax bacteria remain in patients from both treated and controlled groups.

Therefore, the mortality rate of the ciprofloxacin-treated patients can be estimated from the mortality rate of the controlled patients, if the duration of exposure to the anthrax bacteria in the former can be determined from the bacteria eradication rate of the ciprofloxacin regimen.

It has been unexpectedly discovered, during the investigations of the mortality rate of various ciprofloxacin regimens for treating anthrax-exposed patients, that the mortality rate among patients is highly variable depending on the patient characteristics. It has also been discovered that, the mortality rate of anthrax in certain patient populations can be reduced by up to 2 folds, compared to the treatment effects of the currently recommended regimens, if the patients are treated with an optimized ciprofloxacin regimens. It has further been discovered that the optimal ciprofloxacin regimen for treating anthrax is between 625 mg to 1500 mg twice daily oral dose for some patient populations and the precise optimal regimen is dependent on the patient's characteristics.

The mortality rate is equal to (1−survival rate).

BRIEF DESCRIPTION OF THE DRAWINGS

FIG. 1 shows the survival curves of patients in the Sverdlovsk anthrax outbreak in 1979 [Meselson et al, 1994], patients in the US bioterrorism attacks in 2001 [CDC MMWR Weekly, 2001], and monkey in the control group of an animal experiment [Friedlander et al, 1993].

FIG. 2 shows the distribution of onset-to-treatment time in the Sverdlovsk [Walker, 2000] and US patients [CDC MMWR Weekly, 2000].

FIG. 3 shows the bacteria eradication rate after 1 to 10 days of ciprofloxacin treatment as a function of AUC/MIC values, independent of the type of organisms [Forrest et al, 1993(b)].

FIG. 4 shows the estimated distribution of AUC/MIC (based on population model described by Equation 3) for a population with age=30 year and body weight=70 Kg, following 500 mg bid ciprofloxacin oral doses.

FIG. 5 shows the estimated overall survival rates on day 10 after disease onset in a typical patient population (age=40–79 year and BW=50–90 KG), compared with the historical data. The historical data consist of the overall survival data of the victims in the US bioterrorism attacks (FIG. 1) with the average onset-to-treatment time=4 days (FIG. 2); the overall survival rate of the patients in the Sverdlovsk outbreak (FIG. 1), assuming no effective treatment was given (onset-to-treatment>8 days); the survival rate of monkeys [Friedlander et al, 1993] with comparable ciprofloxacin plasma concentration (treatment initiated on day 0); and the 6-point running average of the US data.

FIG. 6 shows the estimated overall survival rates on day 10 after disease onset in patients with age equal to 30 year, body weight ranging from 60 to 130 Kg, following various twice daily (bid) dose regimens of ciprofloxacin initiated from 0 to 5 days after the disease onset.

DETAILED DESCRIPTIONS OF THE INVENTION

The present invention provides new methods for optimizing the therapeutic outcomes of ciprofloxacin treatment for anthrax-exposed patients according to the patients' characteristics. The invention also provides new methods for selecting effective ciprofloxacin treatments and targeting the survival outcomes of ciprofloxacin treatment for anthrax-exposed patients according to the patients' characteristics.

A. Anthrax and Its Treatments

Anthrax is a zoonotic infection that has been recognized as a human disease for thousands of years. Cutaneous, gastrointestinal, and inhalational forms of infection with *Bacillus anthracis* have been traditional associated with agricultural or industrial exposures. There have been several documented anthrax outbreaks in the recent history, such as those in Sverdlovsk 1979 [Meselson et al, 1994] and in the US 2001 [CDC MMWR Weekly, 2001]. This invention will be applied to the most lethal form of anthrax infections—inhalation.

Ciprofloxacin is currently recommended as one of the treatments for anthrax. The effectiveness of the treatment has been previously demonstrated primarily based on an experiment conducted in Rhesus Monkeys [Friedlander et al, 1993; Kelly et al, 1992; Physician's Desk Reference 2001]. In the animal experiment, groups of 10 monkeys were exposed to a lethal aerosol dose of *Bacillus anthracis* spores. One day after the exposure, the animals were treated with the antibiotic continuously for 30 days. The antibiotic regimen provided sufficient protection to the animals while on therapy. The peak and trough plasma concentrations of the antibiotics were obtained from the animals after multiple doses [Kelly et al, 1992]. The required dose regimens of ciprofloxacin [Physician's Desk Reference, 2001] in human for treating anthrax were estimated so that the regimens will produce similar plasma drug concentration in human to those in the animal experiment.

In the previous art, human survival data of anthrax-exposed patients, human pharmacokinetics, and human ciprofloxacin pharmacodynamics information have not been fully utilized to optimize the therapeutic outcomes of ciprofloxacin treatment. Even with the fact that the effectiveness of ciprofloxacin against most other infectious organisms is over 80% [Physician's Desk Reference, 2001] at the recommended doses, the survival rate of anthrax patients treated with the drug remains relatively low (50~60% in the US 2001 outbreak [CDC MMWR Weekly, 2001]). Since anthrax is a fatal disease, dose adjustment based on patient characteristics may have clinically significant impacts on the patient survival.

The inventor has developed novel methods for predicting the survival rate of patients infected with anthrax as a function of the patient characteristics. The methods utilizes the existing human pharmacokinetics and pharmacodynamics data of ciprofloxacin, and the survival rate of patients in an anthrax outbreak in Sverdlovsk 1979. The methods first estimates the percentage of patients with complete anthrax bacteria eradication as a function of time after treatment initiation, with the eradication rate stratified by the pharmacodynamic marker, AUC/MIC. The time to bacteria eradication is then correlated to the patient survival rate based on documented human survival data following the historical anthrax outbreak. The pharmacodynamic marker is highly variable among patients, influenced by the patient characteristics, such as body weight, renal function, age, and gender. Another critical factor affecting the survival rate is the disease onset-to-treatment time. The method adequately predicted the overall survival rate of the victims in the recent bioterrorism attacks in the US 2001.

The present invention was developed from a series of investigations based on the aforementioned new methods. As a result of these investigations, it was unexpectedly discovered that certain dose regimens of ciprofloxacin provide significantly better effectiveness than the previously recommended 500 mg twice daily regimen for treating anthrax in some patient populations. These investigations are described in the following sections (Sections B–H).

B. Survival Rate of Controlled Patients Treated with Placebo or Inactive Treatments or Receiving no Treatment An investigation determined the survival rate of the controlled patients who contract anthrax and receive no effective treatment, with the survival rate as a function of time after disease onset.

The survival rate is defined as the percentage or the ratio of the patients who survive a disease, relative to the total number of patients contracting the disease. The mortality rate is usually defined as the percentage or the ratio of the patients who die from a disease, relative to the total number of patients contracting the disease. Thus, the mortality rate is equal to (1−survival rate).

Figure 1:
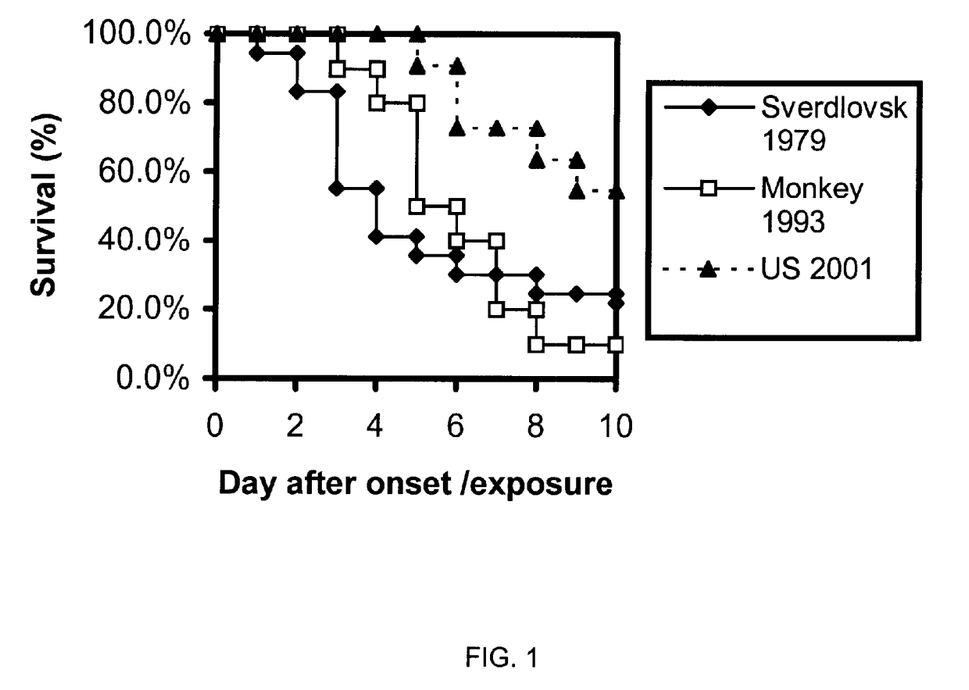

Survival data of human and monkeys exposed to anthrax are available in the literature (FIG. 1). The survival rates of anthrax-exposed Rhesus monkeys were reported [Friedlander et al, 1993] for those treated with 125 mg bid ciprofloxacin and placebo. In this study, groups of 10 monkeys were exposed to a lethal aerosol dose of *Bacillus anthracis* spores. One day after the exposure, the animals were treated with the antibiotics or placebo continuously for 30 days. The group of animal treated with ciprofloxacin were adequately protected from the disease, while the survival rate was 10% for the control group 10 days after the anthrax exposure (FIG. 1).

During the Sverdlovsk anthrax outbreak in 1979 [Meselson et al, 1994], there were 79 documented patients infected with inhalational anthrax, and out of these 79 patients, 68 died [Inglesby et al, 1999]. Out of the 68 deaths, 50 had documented onset-to-death time. The survival rates are presented in FIG. 1. The onset-to-treatment time is available in 21 patients [Walker, 2000], and it is plotted in FIG. 2.

Figure 2:
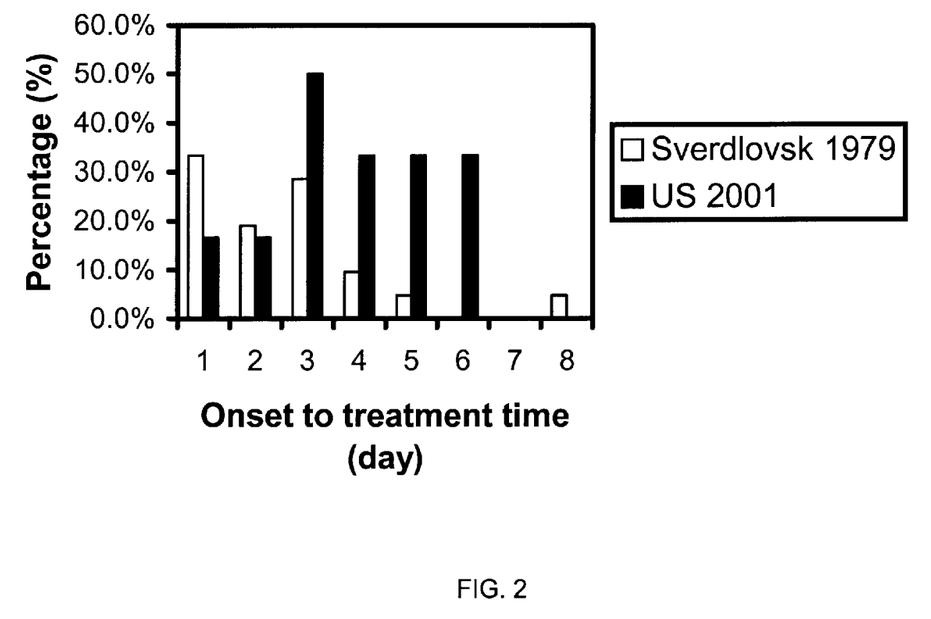

There were 11 confirmed inhalational anthrax cases in the bioterrorism attacks in the US from Oct. $1^{st}$ to Nov. $30^{th}$, 2001 [CDC MMWR Weekly, 2000]. Five out of the 11 patients died before December 31. The onset-to-death time is available in all patients [CDC MMWR Weekly, 2000]. The survival rate of these US patients is shown in FIG. 1. The onset-to-treatment time is available in all US patients and the distribution is shown in FIG. 2.

It appears that the survival rate of the patients in the Sverdlovsk outbreak was similar to or slightly lower than the survival rate of the monkeys in the controlled group of the 1993 experiment. The Sverdlovsk patients were reportedly treated with penicillin, cephalosporin, chloramphenicol, anti-anthrax globin, corticosteroids, osmo-regulatory solutions, and artificial respiration. However, the exact dose regimens were not clearly described in the original paper [Meselson et al, 1994]. Out of the 68 deaths in the Sverdlovsk outbreak, 21 had documented onset-to-treatment time (FIG. 2), which did not show any significant treatment delay compared to the US data. The overall mortality rate of the Sverdlovsk patients (86%) was also similar to the occupationally acquired cases in the US (89%) [Inglesby et al, 1999], the later mostly occurring before the advent of antibiotics. Based on the fact that survival rate in the Sverdlovsk outbreak was similar to those of the animal controlled group and to the occupationally acquired cases without antibiotic treatment, it is apparent that the antibiotic treatment given to the Sverdlovsk patients was ineffective. Thus, the survival curve from the Sverdlovsk patients was treated as one obtained from an inactive controlled group.

The survival rate from the controlled patients can be expressed by the following empirical equation:

$$\text{Survival rate up to day } i = S_i\% \quad (1)$$

where day i is the day after the disease onset, which ranges from 1 to 10 days. Day 0 is the day of disease onset.

The overall survival of the US patients was 55% up to Dec. 31, 2001. This survival rate is significantly higher than that of the Sverdlovsk patients [Meselson et al, 1994], but lower than the ciprofloxacin-treated animals (90% for intend-to-treat) [Friedlander et al, 1993]. It appears that at least ciprofloxacin was given to these patients, perhaps in combination of other antibiotics [CDC MMWR Weekly, 2000].

C. Correlation Between Bacteria Eradication Rate and Pharmacodynamic Marker of Ciprofloxacin Another investigation utilized the pharmacodynamic marker of ciprofloxacin to predict the anthrax bacteria eradication rate in anthrax-exposed patients who receive ciprofloxacin treatments.

A number of pharmacodynamics biomarkers for the efficacy of antibiotics have been defined in the literature [Sanchez-Navarro et al, 1999; Hyatt et al, 1995] that consider microbiological and pharmacokinetic parameters together. These biomarkers are intended for evaluating the potential efficacy of antimicrobial treatments that is correlated to the values of the biomarkers. The pharmacodynamic biomarkers most studied and recommended as predictors of the response to anti-infective therapies include:

Cmax/MIC: The ratio of the maximum plasma drug concentration to the minimum inhibitory concentration.

AUC/MIC: The ratio of the area under the plasma drug concentration curve to the minimum inhibitory concentration.

Tmic: Time for which the plasma drug concentration exceeds MIC.

$AUC_{>mic}$: Area under the drug concentration curve for which the concentration exceed MIC.

PK variable: Other pharmacokinetic parameters that are derived from the antibiotic plasma concentration.

The AUC/MIC ratio of ciprofloxacin has been correlated to the bacteria eradication rate [Forrest et al, 1993(b)]. The inventor contemplates that the bacteria eradication rate can be an influential parameter for successful treatments of anthrax, since the survival rate of anthrax-culture-positive patients reduces drastically as a function of time. An adequate AUC/MIC ratio in anthrax-exposed patients should provide rapid bacteria kill and prevent fatality that may take place within days due to the toxin excreted by the organism. The relatively low survival rate (50~60% in the US 2001 outbreak) of anthrax patients treated with ciprofloxacin is in part due to the delay of treatments and the fact that a complete bacteria eradication at low AUC/MIC of ciprofloxacin may take more than 10 days [Forrest et al, 1993(b)]. However, most of the anthrax-exposed patients died within 10 days following the disease onset [Meselson et al, 1994]. The between-subject variability in ciprofloxacin pharmacodynamic markers may also play a role in the low survival rate, as the AUC/MIC ratio following the same regimen may be sufficient to produce anthrax bacteria kill in some patients but sub-optimal in others.

The bacteria eradication rate is defined as the percentage or the ratio of the patients that become culture-negative, relative to the initial total number of patients infected with the bacteria. The bacteria eradication rate usually increases with the duration of an antibiotic treatment. The bacteria eradication rate can be obtained from human studies [Forrest et al, 1993(b)], animal studies [Firsov et al, 1997], or in vitro studies [McGrath et al, 1994].

The reported MIC of ciprofloxacin against anthrax varies from 0.06 μg/mL to 0.08 μg/mL [Friedlander et al, 1993; Physician's Desk Reference, 2001]. A mid point of 0.07 μg/mL was adopted in the models used by the present invention. It has been demonstrated [Forrest et al, 1993(b); MacGowan et al, 1999; Firsov et al, 1997] that the AUC/MIC values of ciprofloxacin is a good surrogate for bacteria eradication rate. It is also suggested [Firsov et al, 1998] that the correlation between the antimicrobial effects of ciprofloxacin and AUC/MIC is independent of organism species, gram positive or gram negative. The bacteria eradication rate increases with time and is correlated with the AUC/MIC values (FIG. 3) for both gram positive and negative bacteria as shown in a literature study [Forrest et al, 1993(b)], which includes both types of bacteria with a MIC range (0.008–0.4 μg/mL) covering that of anthrax. As the patient fatality occurs rapidly after the onset of anthrax, it is critical to treat the patients with the ciprofloxacin regimens producing adequate AUC/MIC values. For the treatment regimens producing AUC/MIC<125, more than 60% of the anthrax-exposed patients may remain culture-positive after 10 days, which is not acceptable for treating the fatal disease, of which the average onset-to-death time is 3 days. Literature data [Forrest et al, 1993(b); Craig, 1998; Bedos, 1998] also show that the survival rates of human and animals infected with other bacteria are correlated to AUC/MIC values of ciprofloxacin and other fluoroquinolones that are used for treating the infections.

The relationship between AUC/MIC values and the percentage of anthrax-exposed patients with blood culture remaining positive on day i after the treatment initiation can be expressed by the following empirical equation:

$$\text{Percentage of culture-positive patients on day } i = CP_{<125,i}\% \text{ if } AUC/MIC < 125$$

$$\text{Percentage of culture-positive patients on day } i = CP_{125\text{-}250,i}\% \text{ if } 125 < AUC/MIC < 250$$

$$\text{Percentage of culture-positive patients on day } i = CP_{250,i}\% \text{ if } AUC/MIC > 250 \quad (2)$$

where day 1 is the first day of treatment.

D. Correlation between Pharmacodynamics Marker, Patient Characteristics, and Dose Regimen An investigation further utilized various patient characteristics to predict the pharmacodynamics markers of ciprofloxacin. The patient characteristics include age, gender, body weight, ethnicity, serum creatinine, and creatinine clearance. The correlation between pharmacodynamic marker, patient characteristics and dose regimen, can be described by population pharmacokinetic models or other empirical expressions.

The following two-compartment model ciprofloxacin pharmacokinetics was developed based on literature data [Forrest et al, 1993(a), Breilh et al, 2001; Terzivanov et al, 1998; Levey et al 1999; Lewis et al, 2001; Jones et al, 1998]:

$$\frac{dC_1}{dt} = -(k_{el} + k_{12})C_1 + k_{21}C_2, \quad C_{1,i} = f \cdot C_1 + \varepsilon_{cl,i} \quad (3)$$

$$\frac{dC_2}{dt} = k_{12}C_1 - k_{21}C_2, \quad C_{2,i} = C_2 + \varepsilon_{c2,i}$$

$$k_{el} = \frac{CL_t}{V_1}, \quad K_{12} = \frac{CL_d}{V_1}, \quad K_{21} = \frac{CL_d}{V_2}$$

$$V_1 = V_{1,ty} + \eta_{v1}, \quad V_2 = V_{2,ty} + \eta_{v2},$$

$$CL_d = CL_{d,ty} + \eta_{cld}, \quad CL_t = CL_{t,ty} + \eta_{clt}$$

$$CL_{t,ty} = (\theta_1 \cdot CL_{cr} + \theta_2) \cdot BW, \quad V_{1,ty} = \theta_3 \cdot BW, \quad V_{2,ty} = \theta_4 \cdot BW$$

$$CL_{cr} = func(\text{age, gender, body weight, ethnithity}) + \eta_{cclcr}$$

where $C_1$ is the plasma concentration, $C_2$ is the concentration in the peripheral compartment, f is a factor accounting for oral bioavailability, $k_{e1}$ is the elimination rate constant from the central compartment, $k_{12}$ and $k_{21}$ are the distribution rate constants between the central and peripheral compartments, $CL_t$ is the total clearance, $CL_d$ is the distribution clearance, $V_1$ is the central compartment volume of distribution, $V_2$ is the peripheral compartment volume of distribution, $CL_{cr}$ is the creatinine clearance of the patient and is a function of the patient's characteristics, BW is the body weight of the patient, θ represents the covariate model parameter, η represents the between-subject variability, ε represents the within-subject variability and the residual error of the model, i denotes the individual values, and ty denotes the typical population values.

Figure 4:
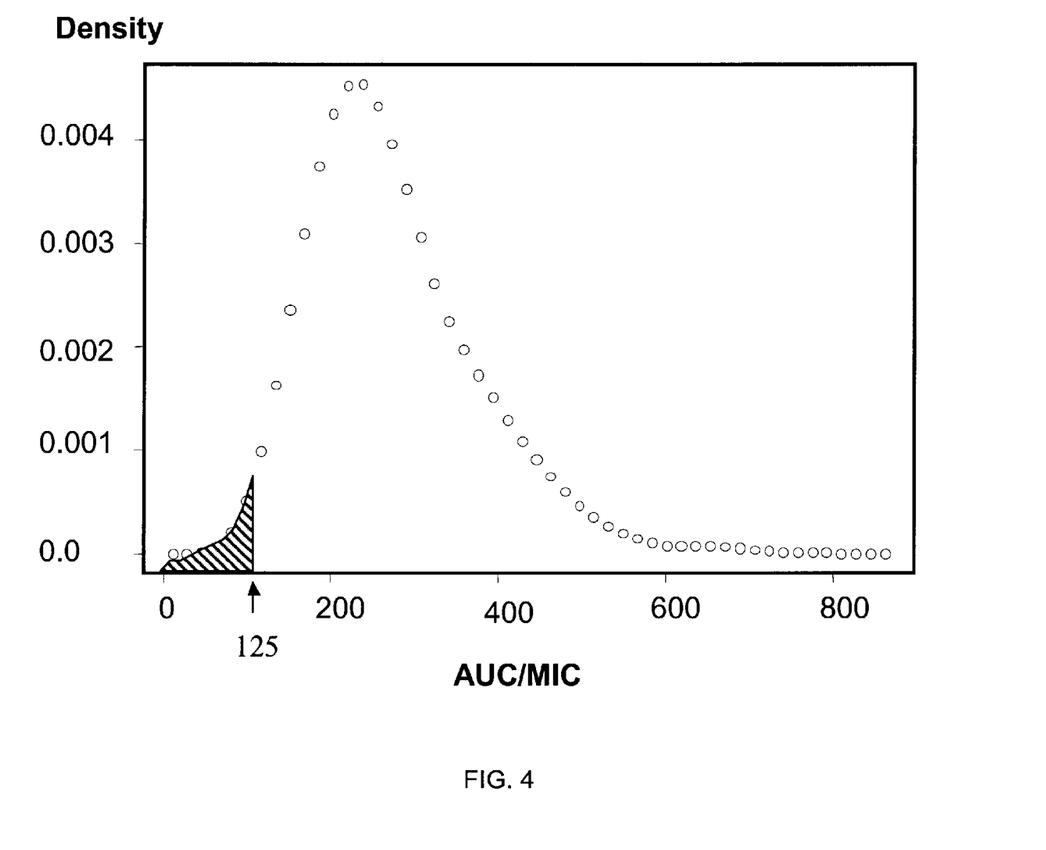
Figure 5:
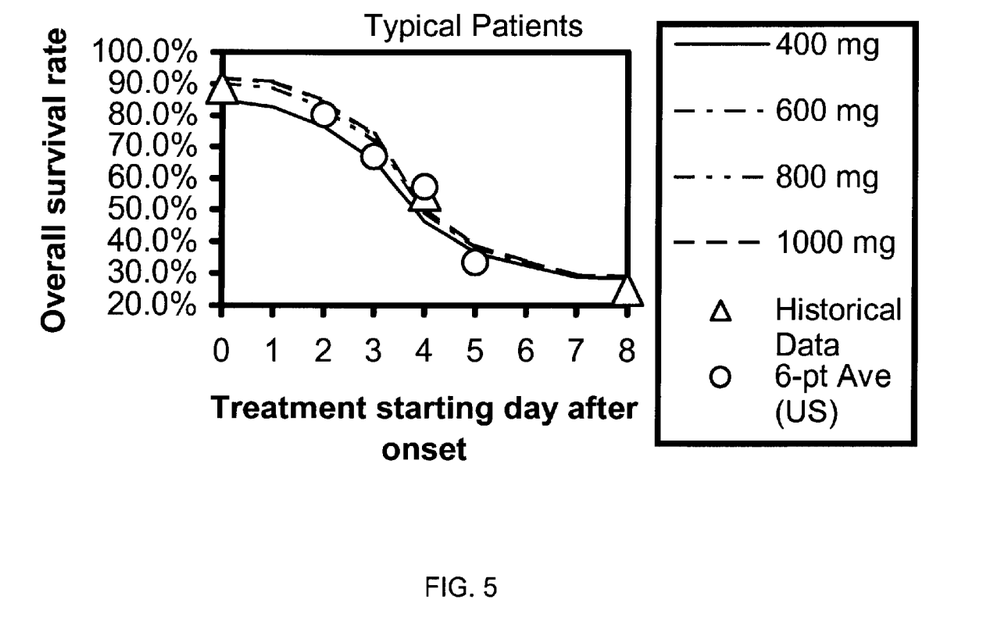
Figure 6:
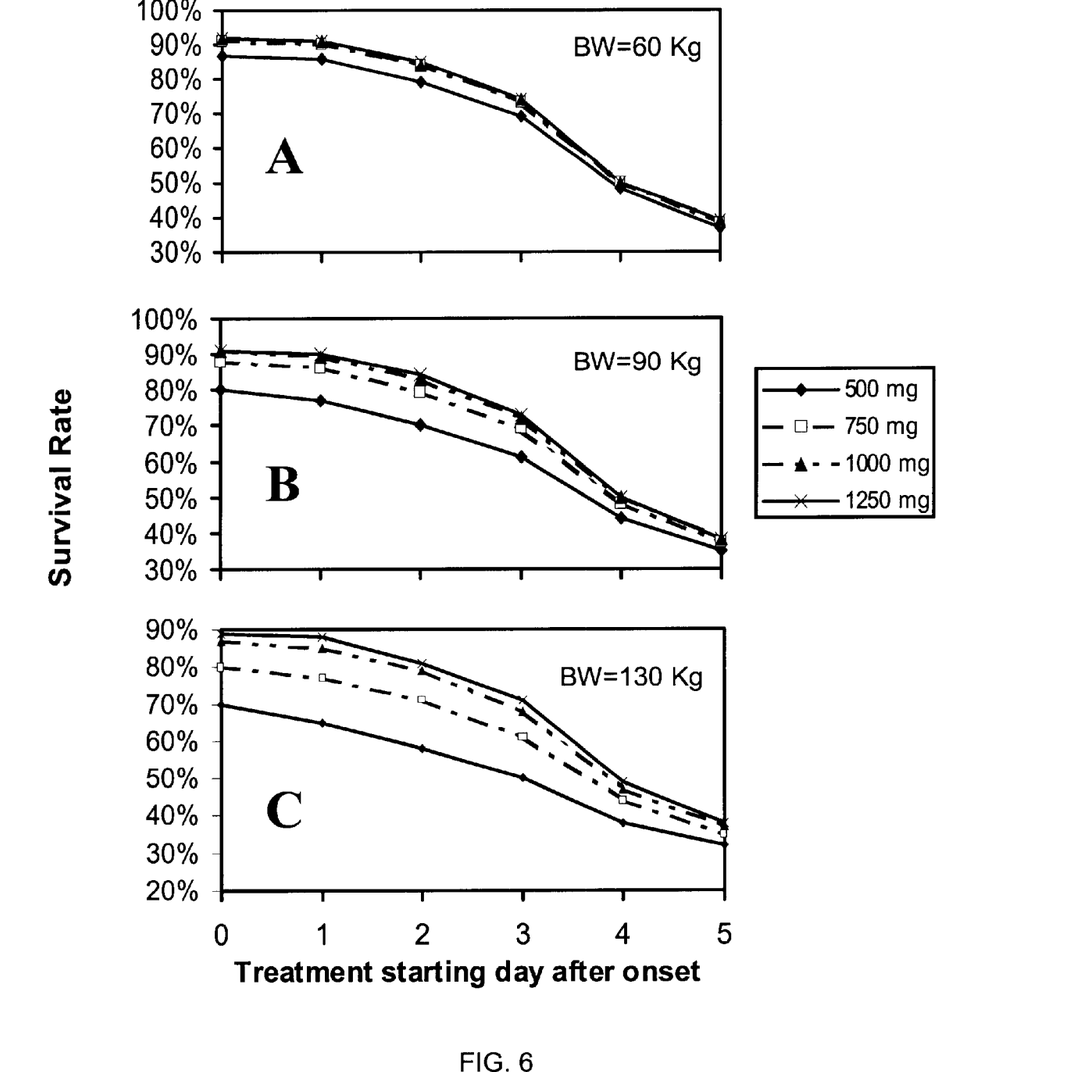

The population-mean of a pharmacodynamic marker, such as AUC/MIC, can be estimated from Equation 3, given the patient characteristics of the population. The population-distribution of the pharmacodynamic marker in the typical population can also be estimated, based on the between-subject and within-subject variability. The Monte-Carlo simulation technique [Lee, 2001] can be used to estimate the population distribution of the pharmacodynamic marker. An example of the population distribution of AUC/MIC is shown in FIG. 4, where the patient population, with age=30 year and body weight=70 Kg, is given 500 mg bid ciprofloxacin oral regimen. The distribution of the steady-state pharmacodynamic marker $AUC_{24h}/MIC$ for 1000 such patients is shown in the plot. The percentage of the patients with AUC/MIC<125 following the dose regimen can be calculated as the ratio of the area under the curve where AUC/MIC<125 (the shaded area in the plot) to the total area under the distribution curve. Similarly, the percentages of the patients with 125<AUC/MIC<250 or AUC/MIC>250 can be estimated from the distribution profile in FIG. 4. The patient distribution with various AUC/MIC values can be expressed by the following empirical equation:

Percentage of patients with $AUC/MIC<125=P_{AUC/MIC<125}\%$

Percentage of patients with $125<AUC/MIC<250=P_{125<AUC/MIC<125}\%$

Percentage of patients with $AUC/MIC>250=P_{AUC/MIC>125}\%$ (4)

Figure 3:
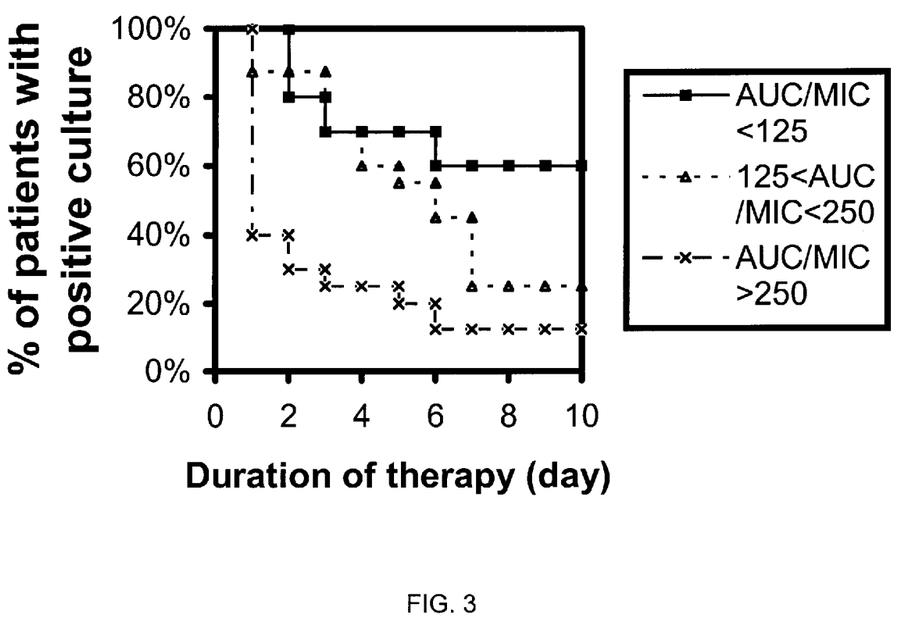

The percentage of patients with positive culture after the treatment initiation for patient groups with different AUC/MIC is shown in FIG. 3. The overall percentage of patients with positive culture after a specific time, day i, following the treatment initiation can then be calculated as follows:

$$\% \text{ patients with positive culture on day } i = \sum_{j=1,3} P_j \cdot CP_{j,i} \quad (5)$$

where j=1 to 3, corresponding to AUC/MIC<125, 125<AUC/MIC<250, and AUC/MIC>250 respectively, and CP and P are defined in Equations (2) and (4).

E. Correlation Between Patient Survival, Bacteria Eradication Rate, and Antibiotic Regimen The probability of patient survival on day i into the ciprofloxacin treatment, which is initiated on day j after the disease onset, can be determined based on the following Equation:

% surviving and culture positive patients in Group k on day i (6)
after treatment initiation = $SCP_{i,k} \% = P_k \cdot SCP_{i-1,k} \frac{CP_i}{CP_{i-1}} \frac{S_{i+j}}{S_{i+j-1}}$ % death occur in Group k on day i after treatment initiation =

$$D_{i,k} \% = P_k \cdot SCP_{i-1,k} \frac{CP_i}{CP_{i-1}} S_{i+j-1} - \frac{S_{i+j}}{S_{i+j-1}}$$

Overall survival rate for treatment initiated on day j after disease onset $= S_{j-1} - \sum_k \sum_i D_{i,k}$ where S, CP, and P are defined in Equations 1, 2, and 4 respectively, k denotes the patients group defined by AUC/MIC ranges in Equations 2 and 4, $Cp_i/Cp_{i-1}$ is the ratio of patients remaining culture positive from day i−1 to i after treatment initiation, and $S_{i+j}/S_{i+j-1}$ is the ratio of culture-positive patients (inactive control) remaining alive from day i+j−1 to i+j after disease onset. The basic assumption for the above equation is that the probability of survival for a culture-positive patient on day (i+j) after disease onset is the same as the survival rate of the control group without effective treatment on the same day after disease onset. The assumption is based on the observation that even a small amount of bacteria level (10 cfu/mL) [Friedlander et al, 1993] may cause death in animals. Bacteremia at levels of $10-10^5$ cfu/mL was present in the control monkeys before their deaths due to anthrax [Friedlander et al, 1993].

F. Survival Rate by Patient Characteristics, Dose Regimens, and Onset-to-treatment Time An investigation utilized the overall survival model described above (Equations 1–6) to estimate the survival rates of anthrax-exposed patients as a function of patients characteristics and treatment initiation days. The overall survival rate on day 10 after disease onset was estimated as a function of the onset-to-treatment time (0–5 days) for different patient populations defined by their gender, age, and body weight (Table 1). Six dose regimens (625 mg to 1500 mg twice daily) of ciprofloxacin were investigated. All patient populations included in the investigation were assumed to be healthy before contracting anthrax, with normal kidney and liver functions, and normal blood pressure. Based on the result, the survival rate is slight better in the female patients. From the survival data of the controlled patients (FIG. 1) [Meselson et al, 1994], most of the anthrax-exposed patients without proper treatments died within 10 days after the disease-onset; therefore, the ciprofloxacin regimen should be given for at least 10 days. In addition, some patients may have disease onset over 60 days after the initial exposure to the anthrax spores; therefore, the ciprofloxacin treatment can be given to the patients up to 120 days to ensure complete eradication of the anthrax bacteria.

Based on the results shown in Table 1, it is discovered that the survival rate of anthrax-exposed patients can be significantly improved in some populations with a ciprofloxacin regimen between 625 mg and 1500 mg twice daily, compared with the 500 mg twice daily regimen. For example, for a male patient with an age between 20–39 year and a body weight between 110–150 kg, a ciprofloxacin regimen between 625 mg to 1000 mg gives a significant better treatment effect than the 500 mg twice daily regimen. The survival rate of anthrax-exposed patients under prophylaxis treatment is represented by the survival rate that is estimated by assuming the onset-to-treatment time is 0 day.

G. Verification of the Model Predictability of Anthrax Patient Survival Rates.

The survival rates of a typical patient population (typical patients with age between 40–79 year, and body weight between 50–90 Kg) estimated by the aforementioned method, described in sections B–F, are compared with the historical survival data of anthrax-exposed patients (FIG. 5). The historical data shown in FIG. 5 consist of the overall survival data of the victims in the US bioterrorism attacks (FIG. 1) with the average onset-to-treatment time=4 days (FIG. 2); the overall survival rate of the patients in the Sverdlovsk outbreak (FIG. 1), assuming no effective treatment was given (onset-to-treatment>8 days); the survival rate of monkeys (treatment initiated on day 0) [Friedlander et al, 1993] with comparable ciprofloxacin plasma concentration to human; and the 6-point running average of the US data. The running average of survival rate and onset-to-treatment time for every 6 patients in the US 2001 anthrax outbreak was calculated, with the patients ranked in the order of the onset-to-treatment time.

The estimated survival rate of the typical population using the overall survival model (Equations 1–6) are consistent with the historical data (FIG. 5). The consistency between the estimated and the observed survival rates validated the method used in the investigations that leaded to the discoveries in the present invention.

H. Safety of Ciprofloxacin Treatment

The safety of ciprofloxacin treatment was evaluated by examining several pharmacokinetic markers for safety, including Cmax and AUC, where Cmax was the maximum plasma concentration of ciprofloxacin following a dose of the drug, and AUC was the area under the plasma concentration-time curve of ciprofloxacin following a dose of the drug. These biomarkers were determined by the population model (Equation 3) as a function of dose regimen of ciprofloxacin and patient characteristics. The values of the safety biomarkers should fall within the normal range of the ciprofloxacin therapy. If the biomarkers fall outside the upper bound of the normal a range, adverse events associated with ciprofloxacin may occur more than normal.

It was discovered that the following ciprofloxacin regimens are safe:

(a) a regimen up to 750 mg twice daily in patients with an age between 12–19 year and a body weight between 50–70 kg, (b) a regimen up to 1000 mg twice daily in patients with a body weight between 70–110 kg, (c) a regimen up to 1250 mg twice daily in patients with a body weight between 110–150 kg.

TABLE 1

The overall survival rate of anthrax patients on day 10 after the disease onset.

| Patient Characteristics | Onset-to-treatment (day) | Survival Rate (%) 500 mg bid | 625 mg bid | 750 mg bid | 1000 mg bid | 1250 mg bid | 1500 mg bid |
|---|---|---|---|---|---|---|---|
| Gender = M | 0 | 84% | 88% | 90% | 91% | 92% | 92% |
| Age = 12–19 y | 1 | 81% | 87% | 88% | 90% | 91% | 91% |
| BW = 50–70 kg | 2 | 75% | 80% | 82% | 84% | 85% | 85% |
| | 3 | 65% | 70% | 71% | 73% | 74% | 74% |
| | 4 | 46% | 48% | 49% | 50% | 50% | 50% |
| | 5 | 36% | 38% | 38% | 38% | 39% | 39% |
| Gender = M | 0 | 75% | 81% | 84% | 89% | 90% | 91% |
| Age= 12–19 y | 1 | 71% | 79% | 82% | 87% | 89% | 90% |
| BW = 70–110 kg | 2 | 64% | 72% | 75% | 81% | 83% | 84% |
| | 3 | 56% | 62% | 65% | 70% | 72% | 73% |
| | 4 | 41% | 44% | 46% | 48% | 49% | 50% |
| | 5 | 34% | 35% | 36% | 38% | 38% | 38% |
| Gender = M | 0 | 64% | 70% | 77% | 83% | 87% | 89% |
| Age = 12–19 y | 1 | 58% | 65% | 73% | 81% | 85% | 88% |
| BW = 110–150 kg | 2 | 51% | 58% | 66% | 74% | 79% | 81% |
| | 3 | 44% | 50% | 57% | 64% | 68% | 71% |
| | 4 | 35% | 38% | 42% | 45% | 47% | 49% |
| | 5 | 30% | 32% | 34% | 36% | 37% | 38% |
| Gender = M | 0 | 87% | 90% | 91% | 92% | 92% | 92% |
| Age = 20–39 y | 1 | 86% | 88% | 90% | 91% | 91% | 91% |
| BW = 50–70 kg | 2 | 79% | 82% | 84% | 84% | 85% | 85% |
| | 3 | 69% | 71% | 73% | 74% | 74% | 74% |
| | 4 | 48% | 49% | 50% | 50% | 50% | 50% |
| | 5 | 37% | 38% | 38% | 39% | 39% | 39% |
| Gender = M | 0 | 80% | 85% | 88% | 91% | 91% | 92% |
| Age = 20–39 y | 1 | 77% | 83% | 86% | 89% | 90% | 91% |
| BW = 70–110 kg | 2 | 70% | 76% | 79% | 83% | 84% | 84% |
| | 3 | 61% | 66% | 69% | 72% | 73% | 74% |
| | 4 | 44% | 46% | 48% | 50% | 50% | 50% |
| | 5 | 35% | 36% | 37% | 38% | 38% | 39% |

TABLE 1-continued The overall survival rate of anthrax patients on day 10 after the disease onset.

| Patient Characteristics | Onset-to-treatment (day) | Survival Rate (%) | | | | | |
|---|---|---|---|---|---|---|---|
| | | 500 mg bid | 625 mg bid | 750 mg bid | 1000 mg bid | 1250 mg bid | 1500 mg bid |
| Gender = M Age = 20–39 y BW = 110–150 kg | 0 | 70% | 75% | 80% | 87% | 89% | 90% |
| | 1 | 65% | 71% | 77% | 85% | 88% | 89% |
| | 2 | 58% | 64% | 71% | 79% | 81% | 83% |
| | 3 | 50% | 55% | 61% | 68% | 71% | 72% |
| | 4 | 38% | 41% | 44% | 47% | 49% | 49% |
| | 5 | 32% | 33% | 35% | 37% | 38% | 38% |
| Gender = M Age = 40–59 y BW = 50–70 kg | 0 | 88% | 91% | 91% | 92% | 92% | 92% |
| | 1 | 87% | 89% | 90% | 91% | 91% | 91% |
| | 2 | 80% | 83% | 84% | 85% | 85% | 85% |
| | 3 | 70% | 72% | 73% | 74% | 74% | 74% |
| | 4 | 48% | 50% | 50% | 50% | 50% | 50% |
| | 5 | 37% | 38% | 38% | 39% | 39% | 39% |
| Gender = M Age = 40–59 y BW = 70–110 kg | 0 | 86% | 88% | 91% | 92% | 92% | 72% |
| | 1 | 84% | 87% | 89% | 90% | 91% | 67% |
| | 2 | 78% | 80% | 83% | 84% | 85% | 60% |
| | 3 | 67% | 70% | 72% | 73% | 74% | 52% |
| | 4 | 47% | 48% | 50% | 50% | 50% | 39% |
| | 5 | 37% | 38% | 38% | 39% | 39% | 33% |
| Gender = M Age = 40–59 y BW = 110–150 kg | 0 | 72% | 78% | 83% | 87% | 90% | 91% |
| | 1 | 67% | 74% | 81% | 86% | 88% | 90% |
| | 2 | 60% | 68% | 74% | 79% | 82% | 84% |
| | 3 | 52% | 58% | 64% | 69% | 71% | 73% |
| | 4 | 39% | 42% | 45% | 48% | 49% | 50% |
| | 5 | 33% | 34% | 36% | 37% | 38% | 38% |
| Gender = F Age = 12–19 y BW = 50–70 kg | 0 | 86% | 89% | 91% | 92% | 92% | 92% |
| | 1 | 84% | 87% | 89% | 91% | 91% | 91% |
| | 2 | 78% | 81% | 83% | 84% | 85% | 85% |
| | 3 | 68% | 70% | 72% | 74% | 74% | 74% |
| | 4 | 47% | 49% | 50% | 50% | 50% | 50% |
| | 5 | 37% | 38% | 38% | 39% | 39% | 39% |
| Gender = F Age = 12–19 y BW = 70–110 kg | 0 | 78% | 84% | 87% | 90% | 91% | 92% |
| | 1 | 75% | 82% | 85% | 88% | 90% | 90% |
| | 2 | 68% | 75% | 78% | 82% | 84% | 84% |
| | 3 | 59% | 65% | 68% | 71% | 73% | 74% |
| | 4 | 43% | 46% | 47% | 49% | 50% | 50% |
| | 5 | 34% | 36% | 37% | 38% | 38% | 39% |
| Gender = F Age = 12–19 y BW = 110–150 kg | 0 | 67% | 73% | 80% | 86% | 88% | 90% |
| | 1 | 62% | 69% | 77% | 83% | 87% | 89% |
| | 2 | 54% | 62% | 70% | 77% | 80% | 82% |
| | 3 | 47% | 53% | 61% | 67% | 70% | 72% |
| | 4 | 36% | 40% | 44% | 47% | 48% | 49% |
| | 5 | 31% | 33% | 35% | 37% | 37% | 38% |
| Gender = F Age = 20–39 y BW = 50–70 kg | 0 | 90% | 91% | 92% | 92% | 92% | 80% |
| | 1 | 89% | 90% | 91% | 91% | 91% | 78% |
| | 2 | 83% | 84% | 85% | 85% | 85% | 71% |
| | 3 | 72% | 73% | 74% | 74% | 74% | 61% |
| | 4 | 49% | 50% | 50% | 50% | 50% | 44% |
| | 5 | 38% | 38% | 39% | 39% | 39% | 35% |
| Gender = F Age = 20–39 y BW = 70–110 kg | 0 | 80% | 85% | 88% | 91% | 92% | 92% |
| | 1 | 78% | 83% | 87% | 89% | 90% | 91% |
| | 2 | 71% | 77% | 80% | 83% | 84% | 84% |
| | 3 | 61% | 66% | 70% | 72% | 73% | 74% |
| | 4 | 44% | 47% | 48% | 50% | 50% | 50% |
| | 5 | 35% | 37% | 37% | 38% | 38% | 39% |
| Gender = F Age = 20–39 y BW = 110–150 kg | 0 | 70% | 77% | 82% | 87% | 90% | 91% |
| | 1 | 65% | 73% | 80% | 85% | 88% | 90% |
| | 2 | 58% | 67% | 73% | 79% | 82% | 83% |
| | 3 | 50% | 57% | 63% | 68% | 71% | 73% |
| | 4 | 38% | 42% | 45% | 47% | 49% | 50% |
| | 5 | 32% | 34% | 36% | 37% | 38% | 38% |
| Gender = F Age = 40–59 y BW = 50–70 kg | 0 | 89% | 91% | 92% | 92% | 92% | 92% |
| | 1 | 87% | 90% | 90% | 91% | 91% | 91% |
| | 2 | 81% | 83% | 84% | 85% | 85% | 85% |
| | 3 | 70% | 73% | 73% | 74% | 74% | 74% |
| | 4 | 48% | 50% | 50% | 50% | 50% | 50% |
| | 5 | 38% | 38% | 39% | 39% | 39% | 39% |
| Gender = F Age = 40–59 y BW = 70–110 kg | 0 | 87% | 89% | 91% | 92% | 92% | 73% |
| | 1 | 85% | 87% | 90% | 90% | 91% | 69% |
| | 2 | 78% | 81% | 83% | 84% | 85% | 62% |
| | 3 | 68% | 70% | 73% | 73% | 74% | 53% |
| | 4 | 47% | 49% | 50% | 50% | 50% | 40% |
| | 5 | 37% | 38% | 38% | 39% | 39% | 33% |

TABLE 1-continued

The overall survival rate of anthrax patients on day 10 after the disease onset.

| Patient Characteristics | Onset-to-treatment (day) | Survival Rate (%) | | | | | |
|---|---|---|---|---|---|---|---|
| | | 500 mg bid | 625 mg bid | 750 mg bid | 1000 mg bid | 1250 mg bid | 1500 mg bid |
| Gender = F | 0 | 73% | 79% | 84% | 88% | 90% | 91% |
| Age = 40–59 y | 1 | 69% | 76% | 81% | 86% | 89% | 90% |
| BW = 110–150 kg | 2 | 62% | 69% | 75% | 80% | 83% | 84% |
| | 3 | 53% | 60% | 65% | 69% | 72% | 73% |
| | 4 | 40% | 43% | 46% | 48% | 49% | 50% |
| | 5 | 33% | 35% | 36% | 37% | 38% | 38% |

I. An Example

The following example is included to demonstrate the embodiments of the invention for one of many applications. Those of skill in the art should, in light of the present disclosure, appreciate that many changes can be made in the specific embodiments that are disclosed and still obtain a like or similar result without departing from the spirit and scope of the invention.

The present invention provides a method for optimizing ciprofloxacin treatment of anthrax-exposed patients according to the patient's characteristics. The invention is primarily based on the discovery of survival rates in different patient populations following different dose regimens of ciprofloxacin, as listed in Table 1.

An example of survival rates in anthrax-exposed patients on day 10 after the disease onset is shown in FIG. 6. Survival rates of three groups of male patients were included in this example, with body weight equal to 60 Kg, 90 Kg, and 130 Kg respectively, and age equal to 30 year. Four different dose regimens of ciprofloxacin were given to the patients: 500, 750, 1000, and 1250 mg twice daily (bid). The results from this example show that the 60-kg group slightly benefits by an increase in dose from 500 mg to 750 mg bid, while raising the dose further does not increase the survival rate. The 90-Kg group continuously benefits from increasing dose regimens, with the mortality rate on day 0 drops by 2 folds from 20% following 500 mg bid to 10% following 1000 mg bid regimens. The increase in the survival rate of the 130-kg group with increasing dose is even dramatic. The result also indicates a trend of reducing overall survival rate with increasing onset-to-treatment time. The severely ill patients with long onset-to-treatment time may particularly benefit from high ciprofloxacin doses.

REFERENCES

Bedos J, Azoulay-Dupuis E, Moine P, Muffat-Joly M, Veber B, Pocidalo J, and Vallee E, "Pharmacokinetic activities of ciprofloxacin and sparfloxacin in a murine pneumococcal pneumonia model: relevance for drug efficacy", The J of pharmacology and experimental therapeutics, 286: 29–35, 1998.

Breilh D, Saux M-C, Marie P, Vergnaud J-M, Jelliffe R W, "Mixed pharmacokinetic population study and diffusion model to describe ciprofloxacin lung concentration", Computer in Biology and Medicine, 31: 147–155, 2001.

CDC MMWR Weekly, 50 (41–48): 889–1079, 2001.

Craig B, "Pharmacokinetic/pharmacodynamic parameters: rationale for antibacterial dosing of mice and men", Clinical Infectious Diseases, 26:1–12, 1998.

Firsov A A, Vostrov S N, Shevchenko A A, and Cornaglia G, "Parameters of bacterial killing and regrowth kinetics and antimicrobial effect examined in terms of area under the concentration-time curve relationships: action of ciprofloxacin against *Escherichia coli* in an in vitro dynamic model", Antimicrobial Agents and Chemotherapy, 41(6) :1281–1287, 1997.

Firsov A A, Vostrov S N, Shevchenko A A, Zinner S H, Cornaglia G, and Portnoy Y A, "MIC-based interspecies prediction of the antimicrobial effects of ciprofloxacin on bacteria of different susceptibilities in an in vitro dynamic model", Antimicrobial Agents and Chemotherapy, 42(11): 2848–2852, 1998.

Forrest A, Ballow C H, Nix D E, Birmingham M C, "Development of a population pharmacokinetic model and optimal sampling strategies for intravenous ciprofloxacin", Antimicrobial Agents and Chemotherapy, 37(5): 1065–1072, 1993(a).

Forrest A, Nix D E, Ballow C H, Goss T F, Birmingham M C, and Schentag J J, "Pharmacodynamics of intravenous ciprofloxacin in seriously ill patients", Antimicrobial Agents and Chemotherapy, 37(5): 1073–1081, 1993(b).

Friedlander A M, Welkos S L, Pitt M L M, Ezzell J W, Worsham P L, Ross K J, Ivins B E, Lowe J R, Howe G B, Mikesell P, and Lawrence W B, "Postexposure prophylaxis against experimental inhalation anthrax", J of Infectious Diseases, 167: 1239–1242, 1993.

Hyatt J M, McKinnon P S, Zimmer G S, and Schentag J J, "The important of pharmacokinetic/pharmacodynamic surrogate markers to outcome: focus on antibacterial agents", Clin Pharmacokinet, 28(2):143–160, 1995.

Inglesby T V, Henderson D A, Bartlett J G, Ascher M S, Eitzen E, Friedlander A M, Hauer J, McDade J, Osterholm M T, O'Toole T, Parker G, Perl T M, Russell P K, Tonat K, "Anthrax as a biological weapon: medical and public health management", JAMA, 281(18): 1735–1745, 1999.

Jones C A, McQuillan G M, Kusek J W, Eberhardt M S, Herman W H, Coresh J, Salive M, Jones C P, and Agodoa L Y, "Serum creatinine levels in the US populations: third national health and nutrition examination survey", American Journal of Kidney disease, 32(6): 992–999, 1998.

Kelly D J, Chulay J D, Mikesell P, and Friedlander A M, "Serum concentrations of penicillin, doxycycline, and ciprofloxacin during prolonged therapy in rhesus monkeys", J of Infectious Diseases, 166: 1184–1187, 1992.

Lee P, "Design and power of a population pharmacokinetic study", Pharmaceutical Research, 18 (1): 75–82, 2001.

Levey A S, Bosch J P, Lewis J B, Greene T, Rogers N, and Roth D, "A more accurate method to estimate glomerular filtration rate fromserum creatinine: a new prediction equation", Annal of Internal Medicine, 130(6): 461–470, 1999.

Lewis J, Agodoa L, Cheek D, Greene T, Middleton J, O'Connor D, Ojo A, Phillips R, Sika M, and Wright J, "Comparison of cross-sectional renal function measurements in african americans with hypertensive nephrosclerosis and of primary formulas to estimate glomerular filtration rate.", american Journal of Kidney Diseases, 38(4): 744–753, 2001.

MacGowan A P, Wootton M, and Holt A, "The antibacterial efficacy of levofloxacin and ciprofloxacin against *Pseudomonas aeruginosa* assessed by combining antibiotic exposure and bacterial susceptibility", J of Antimicrobial Chemotherapy, 43: 345–349, 1999.

McGrath B J, Kang S L, Kaatz G W, and Rybak M J, "Bactericidal activities of teicoplanin, vancomycin, and gentamicin alone and in combination against *staphylococcus aureus* in an in vitro pharmacodynamic model of endocarditis", Antimicrobial Agents and Chemotherapy, 38(8): 2034–2040, 1994.

Meselson M, Guillemin J, Hugh-Johne M, Langmuir A, Popova I, Shelokov A, Yampolskaya O, "The Sverdlovsk anthrax outbreak of 1979", Science, 226: 1202–1208, 1994.

Physician's Desk Reference, 55$^{th}$ edition, 2001.

Samuel M, Ti T Y, "Interventions for treating melioidosis", Cochrane Database Syst Rev;2:CD001263, 2001.

Sanchez-Navarro A and Recio M M S, "Basis of anti-infective therapy, pharmacokinetic-pharmacodynamic criteria and methodology for dual dosage individualisation", Clin Pharmacokinet, 37(4): 289–304, 1999.

Terzivanov D, Atanasova I, Dimitrova V, "Population pharmacokinetics of ciprofloxacin in patients withliver impairments analyzed by NPEM2 algorithm—a retrospective study", International J of Clinical Pharmacology and Therapeutics, 36(7): 376–382, 1998.

Walker D, "Human pathology inhalational disease", FDA Antiinfective Advisory Committee Meeting, July, 2000.

Which is claimed is:

1. A method for selecting an oral ciprofloxacin regimen that produces treatment effects in survival rate significantly better than a 500 mg twice daily regimen of the same drug for post-exposure prophylaxis treatment or post-disease-onset treatment of anthrax in an anthrax-exposed patient, comprising selecting a regimen wherein:

(a) said patient has an age between 12–19 year and a body weight between 50–70 kg, and said selected oral ciprofloxacin regimen is a dose between 625 mg to 750 mg given twice daily for a treatment period of 10 to 120 days; or (b) said patient has a body weight between 70–110 kg, and said selected oral ciprofloxacin regimen is a dose between 625 mg to 1000 mg given twice daily for a treatment period of 10 to 120 days; or (c) said patient has a body weight between 110–150 kg, and said selected oral ciprofloxacin regimen is a dose between 625 mg to 1250 mg given twice daily for a treatment period of 10 to 120 days; or (d) said patient has an age between 12–39 year and a body weight between 70–110 kg, and said selected oral ciprofloxacin regimen is a dose between 625 mg to 1000 mg given twice daily for a treatment period of 10 to 120 days.

2. A method for selecting an oral ciprofloxacin regimen that produces a treatment effect in survival rate at least 5% better than a 500 mg twice daily regimen of the same drug for post-exposure prophylaxis treatment of anthrax in an anthrax-exposed patient, comprising selecting a regimen wherein:

(a) said patient has an age between 12–19 year and a body weight between 50–70 kg, and said selected oral ciprofloxacin regimen is a dose between 750 mg to 1000 mg given twice daily for a treatment period of 10 to 120 days; or (b) said patient has an age between 12–39 year and a body weight between 70–110 kg, and said selected oral ciprofloxacin regimen is a dose between 625 mg to 1000 mg given twice daily for a treatment period of 10 to 120 days; or (c) said patient has a body weight between 110–150 kg, and said selected oral ciprofloxacin regimen is a dose between 625 mg to 1250 mg given twice daily for a treatment period of 10 to 120 days.

3. A method for providing post-exposure prophylaxis treatment or post-disease-onset treatment of anthrax in a patient with an oral ciprofloxacin regimen that is safe and produces treatment effects in survival rate significantly better than a 500 mg twice daily regimen of the same drug, comprising providing a regimen wherein:

(a) said patient has an age between 12–19 year and a body weight between 50–70 kg, and said oral ciprofloxacin regimen is a dose between 625 mg to 750 mg given twice daily for a treatment period of 10 to 120 days; or (b) said patient has a body weight between 70–110 kg, and said oral ciprofloxacin regimen is a dose between 625 mg to 1000 mg given twice daily for a treatment period of 10 to 120 days; or (c) said patient has a body weight between 110–150 kg, and said oral ciprofloxacin regimen is a dose between 625 mg to 1250 mg given twice daily for a treatment period of 10 to 120 days; or (d) said patient has an age between 12–39 year and a body weight between 70–110 kg, and said oral ciprofloxacin regimen is a dose between 625 mg to 1000 mg given twice daily for a treatment period of 10 to 120 days.

4. A method for providing post-exposure prophylaxis treatment or post-disease-onset treatment of anthrax in a patient with an oral ciprofloxacin regimen that is safe and produces a treatment effect in survival rate at least 5% better than a 500 mg twice daily regimen of the same drug, comprising providing a regimen wherein:

(a) said patient has an age between 12–19 year and a body weight between 50–70 kg, and said oral ciprofloxacin regimen is a dose between 750 mg to 1000 mg given twice daily for a treatment period of 10 to 120 days; or (b) said patient has an age between 12–39 year and a body weight between 70–110 kg, and said oral ciprofloxacin regimen is a dose between 625 mg to 1000 mg given twice daily for a treatment period of 10 to 120 days; or (c) said patient has a body weight between 110–150 kg, and said oral ciprofloxacin regimen is a dose between 625 mg to 1250 mg given twice daily for a treatment period of 10 to 120 days.

5. The method of any one of claims 1–4, wherein said patient is male or female.

6. The method of any one of claims 1–4, wherein said patient has a normal kidney function.

7. The method of any one of claims 1–4, wherein said patient has a normal liver function.

8. The method of any one of claims 1–4, wherein said patient has a normal blood pressure.

9. The method of any one of claims 1–4, wherein said patient is otherwise healthy before exposed to anthrax.

* * * * *